United States Patent
Dykers, Jr.

(10) Patent No.: US 7,377,896 B2
(45) Date of Patent: May 27, 2008

(54) INFLATABLE PENIS RING

(76) Inventor: John R. Dykers, Jr., P.O. Box 565, Siler City, NC (US) 27344

( * ) Notice: Subject to any disclaimer, the term of this patent is extended or adjusted under 35 U.S.C. 154(b) by 0 days.

(21) Appl. No.: 11/491,996

(22) Filed: Jul. 25, 2006

(65) Prior Publication Data
US 2007/0093686 A1    Apr. 26, 2007

Related U.S. Application Data

(60) Provisional application No. 60/728,322, filed on Oct. 20, 2005.

(51) Int. Cl.
*A61F 5/00* (2006.01)
(52) U.S. Cl. ....................................... 600/38
(58) Field of Classification Search ............ 600/38–41; 128/897, 898; 606/201–203, 151, 157, 158
See application file for complete search history.

(56) References Cited

U.S. PATENT DOCUMENTS

| | | | |
|---|---|---|---|
| 3,863,638 A | 2/1975 | Rogers et al. | |
| 4,187,851 A | 2/1980 | Hauser | |
| 4,407,275 A * | 10/1983 | Schroeder | 600/38 |
| 4,960,113 A | 10/1990 | Seeberg-Elverfeldt | |
| 5,163,449 A | 11/1992 | Van Der Valk | |
| 5,370,601 A * | 12/1994 | Collins | 600/41 |
| 5,695,444 A * | 12/1997 | Chaney | 600/38 |
| 5,797,890 A | 8/1998 | Goulter et al. | |
| 6,036,635 A | 3/2000 | Altshuler | |
| 6,659,938 B1 * | 12/2003 | Orlowski et al. | 600/38 |

FOREIGN PATENT DOCUMENTS

GB    2 036 561 A    7/1980

* cited by examiner

*Primary Examiner*—Samuel G Gilbert
(74) *Attorney, Agent, or Firm*—Richard C. Litman

(57) ABSTRACT

The inflatable penis ring is a device facilitating attachment of medical appliances to the penis. The device comprises an annular ring having an internal and external diameter. An array of inflatable balloons is evenly spaced around the internal diameter of the ring. A pressure control is provided to inflate or deflate the array of balloons as desired. Either air or liquid may be employed as an inflation medium. Inflation of the balloons, functions to efficiently and comfortably hold the ring in place on the penis. A rim or sleeve is mounted on the ring. Medical appliances may be attached to the rim.

3 Claims, 4 Drawing Sheets

INFLATABLE PENIS RING

CROSS-REFERENCE TO RELATED APPLICATION

This application claims the benefit of U.S. Provisional Patent Application Ser. No. 60/728,322, filed Oct. 20, 2005.

BACKGROUND OF THE INVENTION

1. Field of the Invention

The present invention generally relates to medical appliances. More specifically, the present invention is drawn to an inflatable penis ring that is positioned at the base of the penis for facilitating attachment of various medical devices thereto.

2. Description of the Related Art

In the treatment of problems associated with the penis, treatment devices must somehow be attached to the penis for proper functioning. For example, catheters of various types, condoms and penile erection devices must often be attached to the penis to drain fluids, enhance erections, or the like. There are many attachment devices that have been developed to address these problems. Pertinent examples of such attachment devices are cited and identified in the accompanying IDS. However, none of the cited and identified attachment devices are considered to disclose an inflatable penis ring structure as will be subsequently described and claimed in the instant invention. Thus, an inflatable penis ring solving the aforementioned problems is desired.

SUMMARY OF THE INVENTION

The inflatable penis ring of the present invention is a device shaped similarly to a doughnut. The device comprises an annular ring having an internal and external diameter. An array of inflatable balloons is evenly spaced around the internal diameter of the ring. Means are provided to inflate or deflate the array of balloons as desired. Either air or liquid may be employed as an inflation medium. Inflation of the balloons functions to efficiently and comfortably hold the ring in place on the penis. A rim or sleeve is mounted on the ring. The rim has an inner diameter that may or may not be coextensive with the internal circumference of the ring. In use, the rim is employed as a mounting adjunct for attachment of various medical appliances such as a vacuum erection tube, a urinary drainage condom catheter, etc.

Accordingly, the inflatable penis ring presents a medical appliance that is efficiently designed, easy to use and versatile in its application. The invention provides for improved elements thereof in an arrangement for the purposes described that are inexpensive, dependable and fully effective in accomplishing their intended purposes.

A clear understanding of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
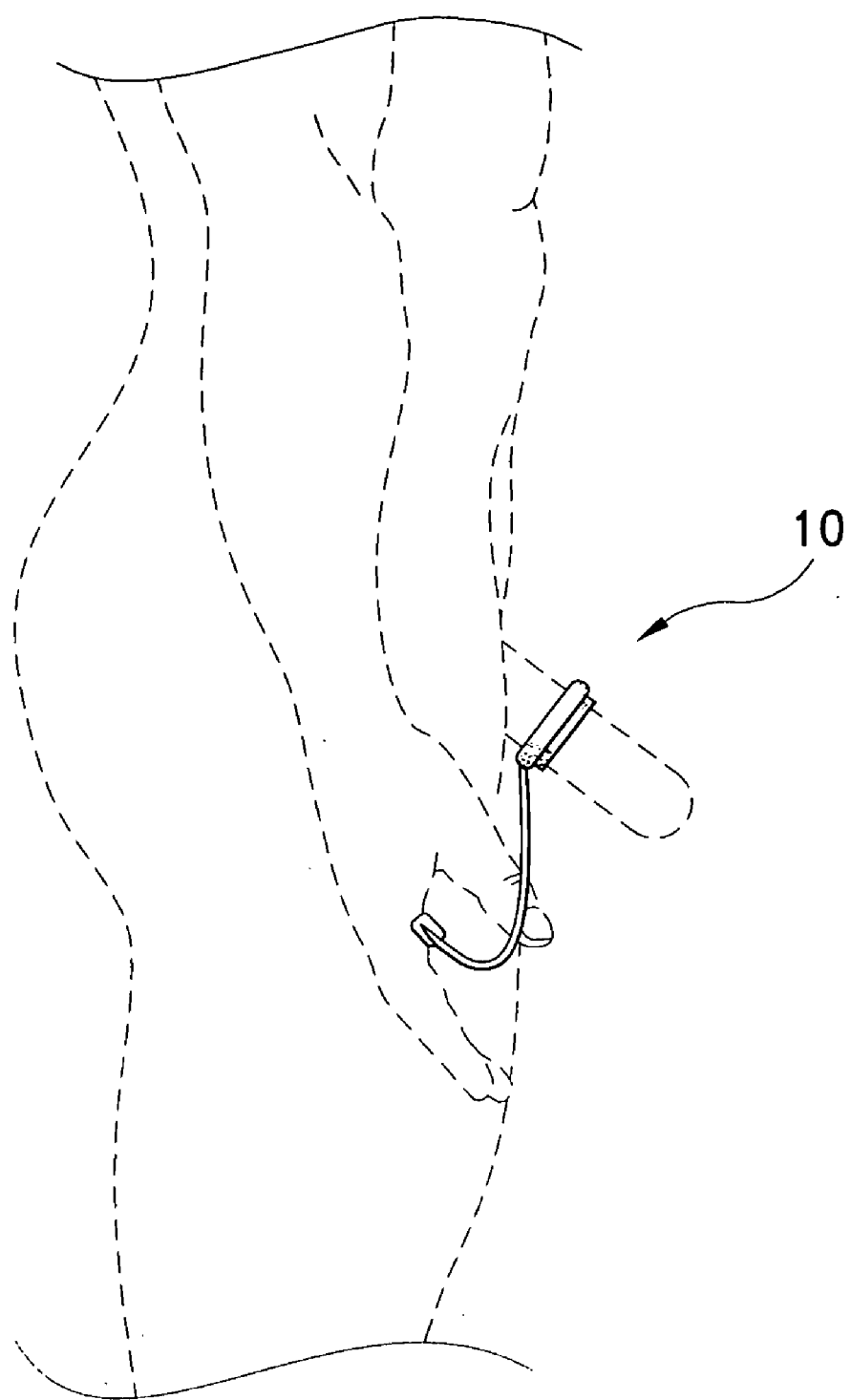
FIG. 1 is an environmental, perspective view of an inflatable penis ring according to the present invention.

Attention is first directed to FIG. 1 wherein the inflatable penis ring of the present invention is generally indicated at 10 and is shown mounted at the base of a patient's penis. In this position, other medical appliances, as indicated above, may be attached to the ring for a desired medical procedure.

Figure 2:
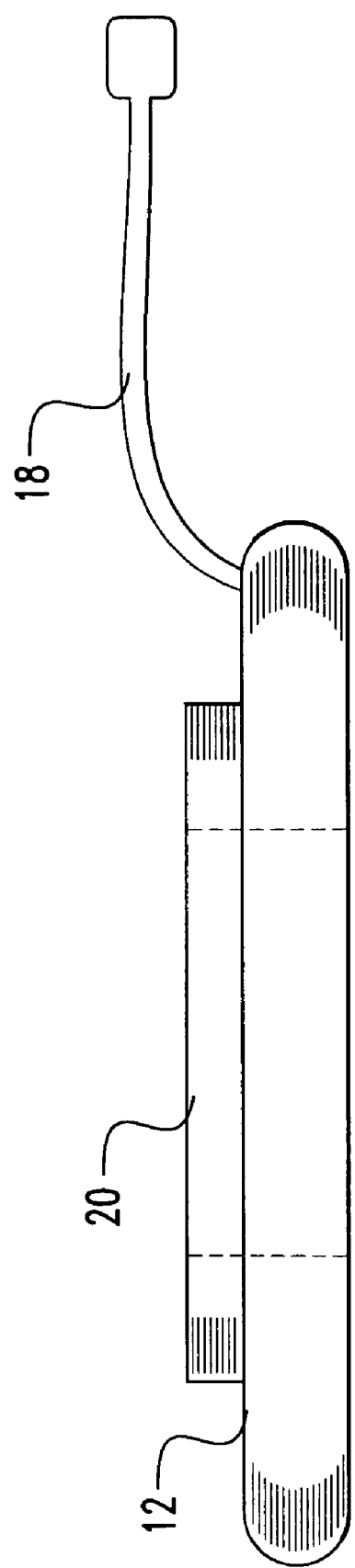
FIG. 2 is a side view of an inflatable penis ring according to the present invention.
Figure 3:
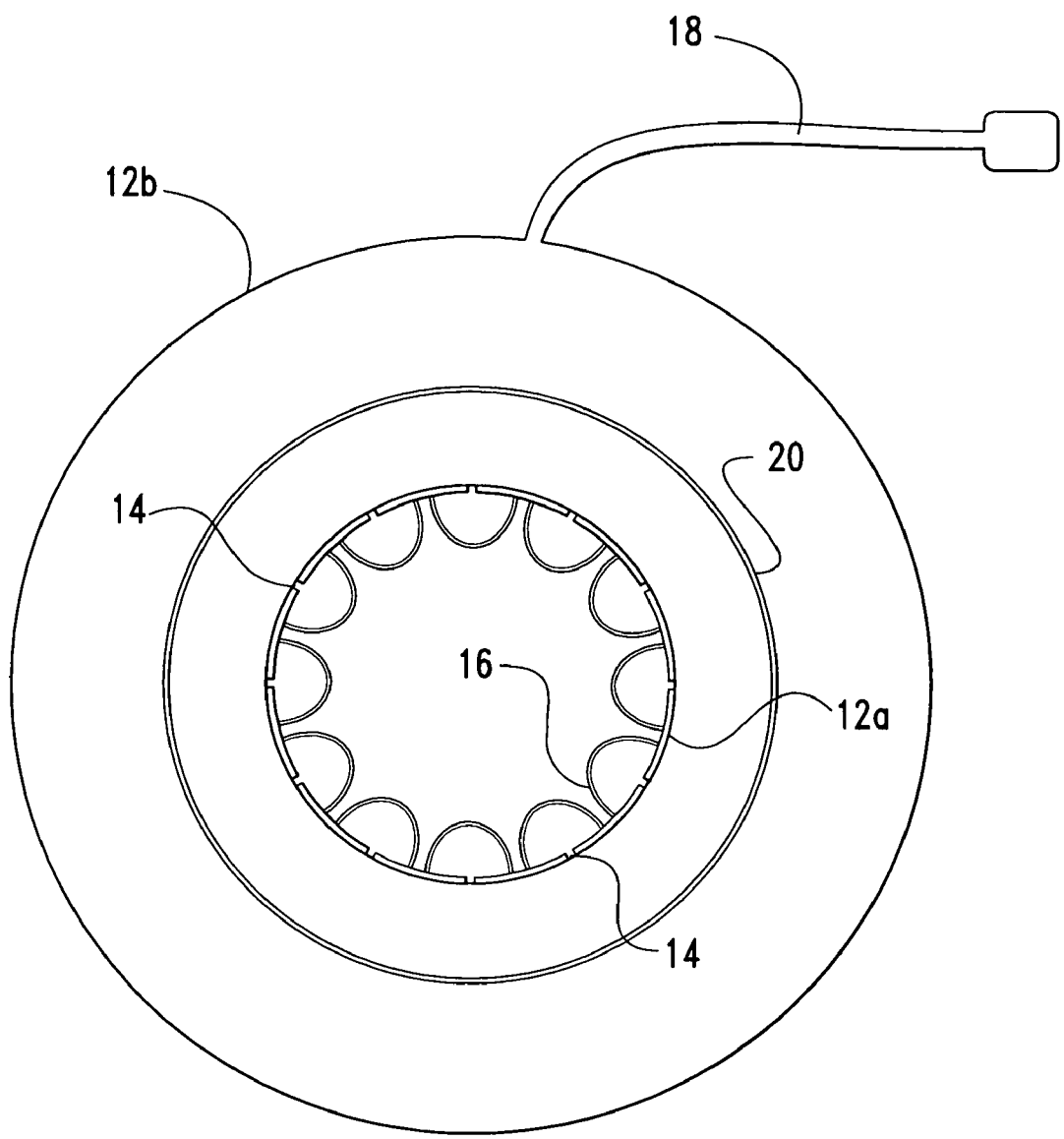
FIG. 3 is a top view of an inflatable penis ring according to the present invention with the balloons in an inflated state.
Figure 4:
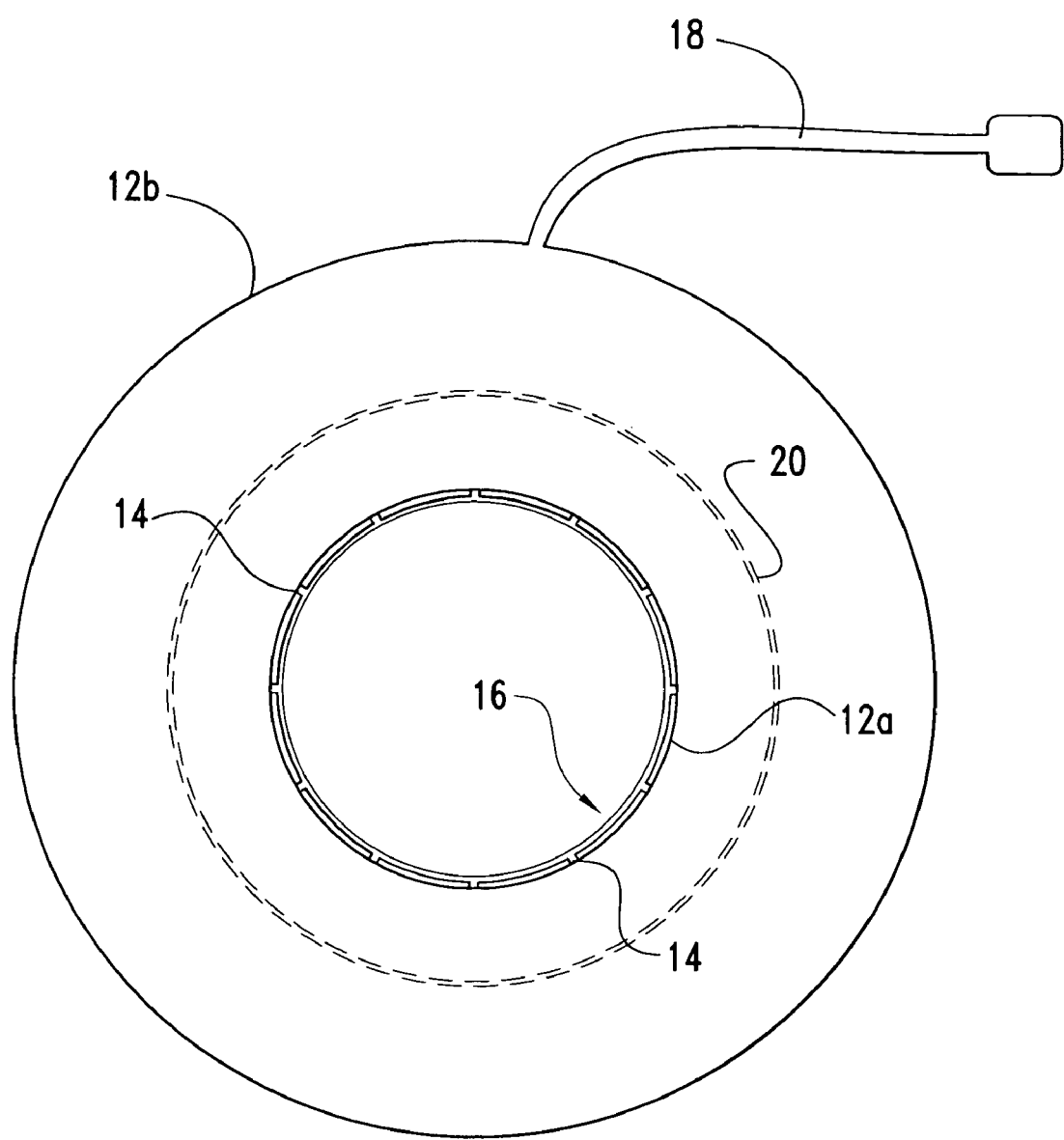
FIG. 4 is a bottom view of an inflatable penis ring according to the present invention with the balloons in a deflated state.

As best seen in FIGS. 2-4, device 10 comprises a hollow ring 12 having wall 12a defining an inner circumference and a wall 12b defining an outer circumference. Hollow ring 12 is fabricated from a relatively rigid material, such as hard rubber. The inner and outer diameters of the ring 12 may vary to accommodate different penis sizes. A series of openings 14 is spaced evenly around the inner circumference 12a. Openings 14 are in fluid communication with the hollow inside of ring 12. Individual balloons 16 are respectively mounted over each opening 14. Connection 18 is provided to control the inflation pressure of the balloons 16. A conventional syringe (not shown) is employed to force fluids (liquid or air) into the hollow ring. A rim 20 is disposed on one exterior sidewall of ring 12 and extends perpendicularly thereabove. Rim 20 is also fabricated from a rigid material. Rim 20 has an inside circumference that may or may not be coextensive with inner circumference 12a. The height of the rim may vary to accommodate standard medical appliances. Although circular as illustrated, it is contemplated that the device could be made to assume other configurations (square, rectangular, hexagonal, etc.).

It is to be understood that the present invention is not limited to the embodiment described above, but encompasses any and all embodiments within the scope of the following claims.

I claim:

1. An inflatable penis ring, comprising:

a ring member having a hollow interior, the ring member having an exterior sidewall and an inner wall, said inner wall defining an inner circumference adapted for insertion over a penis;

an array of openings evenly spaced completely around the inner circumference of the inner wall and opening into the hollow interior;

an array of expandable balloons evenly spaced around said inner wall, each balloon of said array of expandable balloons disposed over a respective opening of said array of openings, wherein said array of expandable balloons when expanded are adapted to engage the penis;

a pressure adjuster attached to the ring member for adjusting pressure in the hollow interior to inflate or deflate the array of expandable balloons; and a rim member positioned on the exterior sidewall of said ring member and extending perpendicularly from the exterior sidewall.

2. The inflatable penis ring according to claim 1 wherein said ring member and said rim member are fabricated from a firm material.

3. The inflatable penis ring according to claim 2 wherein said firm material is firm rubber.

* * * * *